United States Patent
Banzi et al.

[11] Patent Number: 6,124,413
[45] Date of Patent: *Sep. 26, 2000

[54] PROCESS FOR PREPARING ELASTOMERIC EP(D)M COPOLYMERS

[75] Inventors: Viviano Banzi, Vigarano Mainarda; Liliana Gila, Trino; Roberto Santi, Novara; Paolo Biagini, Novara; Giampietro Borsotti, Novara, all of Italy

[73] Assignee: Enichem S.p.A., Milan, Italy

[ * ] Notice: This patent is subject to a terminal disclaimer.

[21] Appl. No.: 08/841,396

[22] Filed: Apr. 30, 1997

[30] Foreign Application Priority Data

May 9, 1996 [IT] Italy .................. MI96A0926

[51] Int. Cl.[7] .................................. C08F 4/42
[52] U.S. Cl. ..................... 526/160; 526/132; 502/155
[58] Field of Search .......................... 526/132, 160

[56] References Cited

U.S. PATENT DOCUMENTS

| | | | |
|---|---|---|---|
| 5,292,845 | 3/1994 | Kawasaki et al. | 526/160 |
| 5,565,533 | 10/1996 | Galimberti et al. | 526/160 |
| 5,610,254 | 3/1997 | Sagane et al. | 526/160 |
| 5,696,213 | 12/1997 | Schiffino et al. | 526/160 |
| 5,696,214 | 12/1997 | Sagane et al. | 526/160 |
| 5,698,651 | 12/1997 | Kawasaki et al. | 526/160 |
| 5,710,223 | 1/1998 | Fukuoka et al. | 526/160 |
| 5,739,366 | 4/1998 | Imuta et al. | 526/160 |
| 5,753,578 | 5/1998 | Santi et al. | 526/160 |
| 5,807,948 | 9/1998 | Sagane et al. | 526/160 |

FOREIGN PATENT DOCUMENTS 0 347 129  12/1989  European Pat. Off. .

OTHER PUBLICATIONS

Taek Kyu Han, et al., American Chemical Society, vol. 28, No. 14, 1995, Ethylene and Propylene Polymerization over Chiral ansa–Dichloro[O–phenylenedimethylenebis(N5–1–indenyl)]zirconium [Zr{C6H4(CH2–1–C9H6)2–1,2}C12].
The Condensed Chemical Dictionary, 9th Ed., Van Nostrand Reinhold Co. N.Y. (1997) p. 552.

Primary Examiner—David W. Wu
Assistant Examiner—Ling-Siu Choi
Attorney, Agent, or Firm—Oblon, Spivak, McClelland, Maier & Neustadt, P.C.

[57] ABSTRACT

Process for preparing elastomeric copolymers of ethylene-propylene (EPM) type and elastomeric terpolymers of ethylene-propylene-diene (EPDM) type with a propylene content comprised within the range of from 15 to 75%, carried out in the presence of metallocenes of formula (I)

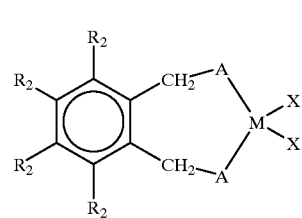

16 Claims, No Drawings

PROCESS FOR PREPARING ELASTOMERIC EP(D)M COPOLYMERS

The present invention relates to a process for preparing elastomeric copolymers of ethylene-propylene (EPM) type and elastomeric terpolymers of ethylene-propylene-diene (EPDM) type.

For the above said copolymerizations, zirconium or titanium complexes are being developed more and more which bear ligands of bis-indenyl type, bis-fluorenyl type or of mixed type, as, e.g., fluorenyl-cyclopentadienyl ligands (P. C. Mohring, N. J. Coville, J. Organomet. Chem. 479, 1, 1994).

Unfortunately, these catalysts display the drawback that not always they give rise to acceptable viscosity values from application viewpoint, in particular when elastomeric copolymers of ethylene-propylene type are prepared with propylene contents comprised within the range of from 35 to 65% by weight, which is that composition range which yields the best results as to elastomeric properties.

It is known as well that in the preparation of EPM or EPDM copolymers, the copolymerization is often performed in the presence of hydrogen as a molecular weight regulant.

However, the use of hydrogen implies sometimes considerable difficulties owing to the high sensibility of the metallocene-based catalytic system to hydrogen. It derives that the hydrogen amounts suitable for regulating the molecular weight are too low to be properly metered.

The Italian Patent Application IT-A-MI 95/A 001444 discloses a new family of metallocenes, in particular o-xylene-α,α'-bisindenyl metallocenes. These metallocenes are prepared by starting from α,α'-dibromo-o-xylene and indene, or its derivatives, in the presence of lithium-butyl. The so obtained o-xylene-α,α'-bis-indenyl is then reacted with $ZrCl_4$, thus giving rise to the above said metallocenes.

The present Applicant found now that some of these metallocenes are particularly useful in the production of ethylene-propylene elastomers with high Mooney viscosity values and make it possible the above drawbacks to be overcome.

In accordance therewith, the present invention relates to a process for preparing elastomeric copolymers of ethylene-propylene (EPM) type and elastomeric terpolymers of ethylene-propylene-diene (EPDM) type with propylene contents comprised within the range of from 15 to 75% by weight, preferably of from 25 to 70% by weight, still more preferably of from 35 to 60% by weight, which comprises the following steps:

1) propylene and optional diene are fed to a polymerization reactor, preferably diluted with a hydrocarbon, still more preferably with a low boiling $C_3$–$C_5$ hydrocarbon, preferably propane, under such a pressure as to allow propylene to be used in liquified form;
2) ethylene is added to the mixture obtained from above step (1) in a sufficient amount for keeping the desired ethylene:propylene ratio in the liquid phase;
3) to the mixture obtained from above step (2), the catalytic system is added which comprises one or more metallocenes having the general formula (I) and one or more co-catalysts selected from (i) compounds with general formula (IV) $(Ra)_xNH_{4-x}B(Rd)_4$, with general formula (V) $(Ra)_3PHB(Rd)_4$, with general formula (VI) $B(Rd)_3$, with general formula (VII) $(C_6H_5)_3CB(Rd)_4$, optionally in the presence of an alkylating agent, (ii) alumoxane;
4) the mixture obtained from above step (3) is caused to react during a long enough time in order to allow the polymerization to take place of the system constituted by ethylene, propylene and optional diene system in order to yield an EP(D)M having a Mooney viscosity ($ML_{1+4}$ at 100° C.) higher than 20, characterized in that the catalytic system comprises at least one metallocene selected from those having the general formula (I)

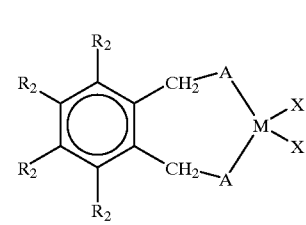

(I)

wherein
M is selected from titanium, zirconium, hafnium;
X is selected from halogen, alkoxy, amido, carboxy, carbamate, alkyl, aryl, hydrogen; preferably, X is selected from halogen, $C_1$–$C_3$ hydrocarbyl radical, hydrogen, still more preferably X is chlorine;
A is a radical of $\eta^5$-indenyl type (Ia) or $\eta^5$-tetrahydroindenyl type (Ib)

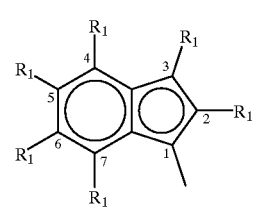

(Ia)

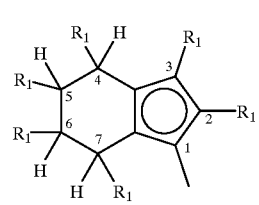

(Ib)

wherein the radicals $R_1$ and $R_2$, which may be the same or different from each other, are selected from H, aliphatic radical, cycloaliphatic radical, aryl radical, preferably from hydrogen, methyl, ethyl, phenyl;
with those compounds in which A is represented by formula (Ia), $R_2$=H and $R_1$ is different from —H in 3-, 4- and 7-positions, being excluded.

According to the preferred embodiment, all $R_2$ are the same and are —H and in A radical the number of R different from —H is equal to, or lower than, 3.

Examples of compounds having general formula (I) with different A radicals and different $R_1$ radicals, which are effective in the process according to the present invention, are:

o-xylene-α,α'-bis-[$\eta^5$-(3-methyl)-inden-1-yl] zirconium dichloride;

o-xylene-α,α'-bis-[$\eta^5$-(5,6-dimethyl)-inden-1-yl] zirconium dichloride;

o-xylene-α,α'-bis-[$\eta^5$-(4,7-dimethyl)-inden-1-yl] zirconium dichloride;

o-xylene-α,α'-bis-[$\eta^5$-(3-methyl)-4,5,6,7tetrahydroinden-1-yl] zirconium dichloride;

o-xylene-α,α'-bis-[η$^5$-(3,5,6-trimethyl)-4,5,6,7-tetrahydroinden-1-yl] zirconium dichloride;

o-xylene-α,α'-bis-[η$^5$-inden-1-yl] zirconium dichloride;

o-xylene-α,α'-bis-[η$^5$-(3,5,6-trimethyl)-inden-1-yl] zirconium dichloride;

o-xylene-α,α'-bis-[η$^5$-(3-ethyl)-inden-1-yl] zirconium dichloride;

o-xylene-α,α'-bis-[η$^5$-(3-phenyl)-inden-1-yl] zirconium dichloride;

o-xylene-α,α'-bis-[η$^5$-4,5,6,7-tetrahydroinden-1-yl] zirconium dichloride;

A typical example of metallocenes which cannot be used in the preparation of EP(D)M according to the present invention is o-xylene-α,α'-bis-[η$^5$-3,4,7-trimethyl-inden-1-yl] zirconium dichloride.

In the copolymerization of ethylene with propylene (and optional diene) the catalytic system additional comprises, besides metallocene of general formula (I), also a further component (which will be referred to herein as "co-catalyst") selected from alumoxane and compounds having the general formula (IV) $(Ra)_xNH_{4-x}B(Rd)_4$ (wherein x is selected from 1, 2 or 3) or (V) $(Ra)_3PHB(Rd)_4$, or (VI) $B(Rd)_3$, or (VII) $(C_6H_5)_3CB(Rd)_4$, which, by reacting with a metallocene having the general formula (I) are capable of generating catalytic systems with ionic character. In the above said compounds having general formula (IV), (V), (VI) or (VII), the Ra groups, which may be the same or different from one another, are monofunctional alkyl or aryl radicals, and Rd's, which may be the same or different from one another, are monofunctional aryl radicals, preferably partially or totally fluorinated, still more preferably totally fluorinated.

The nature of the co-catalyst is known to determine the modalities of preparation of the catalytic system. In the following the general description is supplied of two methods of preparation of the catalytic system, both of which are well known for those skilled in the art.

According to a first method, the catalytic system is prepared by starting from one or more metallocenes of general formula (I) and an alumoxane. Under the general term "alumoxane", an aluminium compound is meant, which can have an either linear or cyclic structure. The linear structure as the general formula (VIII) $(R_e)_2$—Al—O—[—Al—O($R_e$)—O—]$_p$—Al $(R_e)_2$, and the cyclic alumoxanes have the general formula (IX) —[—O—Al $(R_e)$—O—]$_{p+2}$, in which the several $R_e$'s, which may be the same or different from each other, are selected from H, $C_1$–$C_6$-alkyl radicals, $C_6$–$C_{18}$-aryl radicals; "p" is an integer having a value comprised within the range of from 2 to 50, preferably of from 10 to 35. When the several $R_e$'s are all the same, they are selected from methyl, ethyl, propyl, isobutyl, and preferably are methyl.

When the several $R_e$'s are different from one another, they preferably are methyl and hydrogen or, alternatively, methyl and isobutyl, with hydrogen and isobutyl being preferred.

The alumoxane can be prepared according to various methods well known to those skilled in the art. One from these methods comprises, for example, reacting an aluminium alkyl compound and/or an aluminium alkyl hydride with water (either in gas, or solid, liquid or bound form, for example as crystal water) in an inert solvent, for example, toluene. For preparing an alumoxane having different $R_e$ alkyl radicals, two different trialkyl aluminum compounds $(AlR_3+AlR'_3)$ are reacted with water (see S. Pasynkiewicz, Polyhedron 9 (1990) 429–430 and EP-A302,424).

The precise nature of alumoxane is not known, however from the market toluenic solutions of methyl-alumoxane are available, as, e.g., the product Eurecene 5100 10T ex firm Witco), of which the active aluminium concentration is indicated, which makes it very easy to use.

The catalytic system is prepared by adding to the mixture of the thoroughly desiccated monomers, previously charged to the polymerization reactor, a hydrocarbon solution of 10% alumoxane by weight. The resulting mixture is heated up to the desired temperature and then one or more metallocenes are added, which are selected from those with general formula (I), in such an amount as to obtain a total concentration comprised within the range of from $10^{-8}$ up to $10^{-4}$ M according to its activity, and with a molar ratio of aluminium to metallocene comprised within the range of from $5\times10^2$ to $2\times10^4$. In this way, the catalytic system is defined as being "prepared in situ".

According to an alternative procedure, metallocene, or metallocene mixture, can be preactivated with alumoxane before being used in the polymerization step, with its activity being increased by this procedure. In this case, metallocene is dissolved in an inert hydrocarbon solvent, which is preferably either aliphatic or aromatic, still more preferably toluene, so that its concentration is comprised within the range of from $10^{-1}$ up to $10^{-4}$ M. The solution of alumoxane in toluene is then added in such a way that the molar ratio of alumoxane to metallocene is comprised within the range of from $5\times10^2$ up to $2\times10^4$. The components are caused to react during a time comprised within the range of from a few minutes up to 60 hours, preferably of from 5 to 60 minutes, at a temperature comprised within the range of from $-78°$ C. up to $+100°$ C., preferably of from $0°$ C. up to $70°$ C. This route of preparation of the catalytic system is commonly referred to as "preliminary formation". When the preliminary formation time is ended, the reaction mixture is added to the mixture of monomers previously prepared in the polymerization reactor, in such an amount that the end concentration of metallocene in the reaction mixture is comprised within the range of from $10^{-8}$ to $10^{-4}$ moles/litre.

According to a second method, the catalytic system is prepared still by starting from one or more metallocenes with general formula (I) and a co-catalyst with general formula (IV), (V), (VI) or (VII). In this case, the operating modalities depend on the nature of X radicals bound to M in the general formula (I).

With X being equal to H or to an alkyl radical, the catalytic system is prepared by adding one or more metallocenes with general formula (I) to the previously prepared monomer mixture, in such an amount the total concentration is comprised within the range of from $10^{-8}$ up to $10^{-4}$ moles/litre. The mixture is then heated up to the desired temperature and then, as the co-catalyst, a compound is added which is selected from the compounds having general formula (IV), (V), (VI) or (VII), as disclosed in EP-A-277,004; at such a concentration that the total molar ratio to metallocene is comprised within the range of from 0.7 to 3.5.

When X is different from H or a hydrocarbyl radical, the catalytic system will be formed by one or more metallocenes having general formula (I), an alkylating compound selected from trialkylaluminium, dialkymagnesium and alkyllithium, or still other alkylating agents well known to those skilled in the art, and any of compounds of general formula (IV), (V), (VI) or (VII), or a mixture thereof, as disclosed in EP-A-612,769. In order to generate the catalytic system, the metallocene compound having general formula (I) is pre-mixed with the suitable alkylating agent in either aliphatic or aromatic hydrocarbon solvents, or mixtures thereof, at a temperature comprised within the range of from $-20$ to $+100°$ C., preferably of from $0°$ C. to $60°$ C., and still more preferably of from +20° C. to +50° C., during a time comprised within the range of from 1 minute to 24 hours, preferably of from 2 minutes to 12 hours, still more preferably from 5 minutes to 2 hours.

The molar ratio of the alkylating compound and the compound with general formula (I) may be comprised within the range of from 1 to 1000, preferably of from 10 to 500, still more preferably of from 30 to 300.

The mixture is then brought into contact with a compound with general formula (IV), (V), (VI) or (VII) at the temperature indicated above, during a time comprised within the range of from 1 minute to 2 hours, preferably of from 2 minutes to 30 minutes, and the resulting mixture is then fed to the polymerization reactor. The molar ratio of compound with general formula (IV), (V), (VI) or (VII) to metallocene (I) can be comprised within the range of from 0.1 to 10, preferably of from 1 to 3.

Independently of the method used in order to prepare the catalytic system, the reaction between the metallocene with general formula (I) and the cocatalyst can be carried in the presence, or less, of variable amounts of one, or all, of the monomer(s) to be polymerized. In the event small amounts of monomer to be polymerized are present, i.e., with molar ratios of monomer:metallocene comprised within the range of from 10 to 1000, that process takes place which, according to the prior art, is referred to as "prepolymerization", during which small amounts are formed of a solid polymer which embed nearly all the components of the catalytic system. This suspension of polymer/catalytic system displays a still higher catalytic activity, and can be used in order to polymerize large amounts of monomers, with the morphologic characteristics of the resulting polymer being improved.

The catalytic systems according to the present invention are generally used at very low molar concentrations, comprised within the range of from $10^{-8}$ up to $10^{-4}$, as expressed as metallocene of general formula (I). Although they are so diluted, these catalytic systems are characterized by a very high activity, comprised within the range of from 500 to 10,000 kg of polymer per g of transition metal per copolymerization hour. However, in order to obtain this activity levels at the above reported concentrations, the catalytic system must be carefully protected from possibly present catalyst poisons, also at ppm (parts per million parts) levels, in the monomers, above all in propylene, and in the solvents used in the polymerization reaction. This result can be obtained by using, in the polymerization environment, particularly effective substances for removing impurities characterized by the presence of active hydrogens, as trialkylaluminium compounds, in particular trimethylaluminium, triethylaluminium, triisobutylaluminium and diisobutylaluminium monohydride. These substances do not participate directly in the catalytic process, but are capable of effectively capturing the above mentioned poisons, when used at concentrations of about $10^{-3-10-4}$ M in the polymerization environment.

The catalytic system of the present invention can be applied to polymerization reactions in slurry phase (in which a dispersant is used, for example, propane or butane), and to polymerization essentially carried out in the absence of solvents (as solvent-free polymerization in liquid phase). Of course, the catalyst of the invention can be applied to continuous or batchwise polymerization.

When batchwise polymerization is carried out, the reaction time, as a function of temperature and concentration, is generally comprised within the range of from 10 minutes to 10 hours, preferably of from 30 minutes to 120 minutes.

The polymerization temperature is approximately comprised within the range of from −78° C. to 200° C., preferably of from −20° C. to 100° C., still more preferably of from 10° C. to 70° C. No particular limits exist on olefin pressure in the reaction system, although, preferably, the pressure is comprised within the range of from atmopsheric pressure up to 50 kg/cm² G.

In the polymerization process, the molecular weight can be controlled by means of any known methods, for example by suitably selecting polymerization temperature and pressure, and adding hydrogen.

At the end of the polymerization process, the produced elastomer leaving the reactor is recovered in various ways, for example by submitting it to a stripping treatment, preferably with water by steam stripping, in order to remove non-converted monomers and the possibly used diluent. This operation can be followed by a treatment on the extruder, by means of which water and possible residual olefin traces are removed.

When preparing EPDM's is desired, the useful dienes for preparing EPDM terpolymers are selected from:

straight-chain dienes, as 1,4-hexadiene and 1,6-octadiene;

branched dienes, as 5-methyl-1,4-hexadiene; 3,7-dimethyl-1,6-octadiene; 3,7-dimethyl-1,7-octadiene single-ring cyclic dienes, as 1,4-cyclohexadiene; 1,5-cyclooctadiene; 1,5-cyclododecadiene;

dienes with bridge-condensed rings, as dicyclopentadiene; bicyclo[2.2.1]epta-2,5-diene; alkenyl-, alkylidene-, cycloalkenyl and cycloalkylidene norbornenes, as 5-methylene-2-norbornene, 5-ethylidene-2-norbornene (ENB), 5-propenyl-2-norbornene.

Among non-conjugated dienes typically used for preparing these copolymers, those dienes are preferred which contain at least one double bond, in a stretched ring, still more preferably 5-ethylidene-2-norbornene (ENB) and furthermore 1,4-hexadiene and 1,6-octadiene.

In the case of EPDM terpolymers, the amount of dienic monomer should not exceed 15% by weight and should preferably be comprised within the range of from 2 to 10% by weight.

A further object of the present invention are the following metallocenes:

A) o-Xylene-α,α'-bis-[η⁵-(3-methyl)-4,5,6,7-tetrahydroinden-1-yl] zirconium dichloride, i.e., compound of general formula (I) in which $R_2$=H, X=Cl, M=Zr, A has the structure (Ib) in which $R_1$=CH$_3$ in 3-position, $R_1$=H, in all other positions.

B) o-Xylene-α,α'-bis-[η⁵-(3,5,6-trimethyl)-4,5,6,7-tetrahydroinden-1-yl] zirconium dichloride, i.e., compound of general formula (I) in which $R_2$=H, X=Cl, M=Zr, A has the structure (Ib) in which $R_1$=CH$_3$ in 3-, 5- and 6-positions, $R_1$=H, in all other positions.

C) o-Xylene-α,α'-bis-[η⁵-(3-ethyl)-inden-1-yl] zirconium dichloride, i.e., compound of general formula (I) in which $R_2$=H, X=Cl, M=Zr, A has the structure (Ia) in which $R_1$=C$_2$H$_5$ in 3-position, $R_1$=H, in all other positions.

D) o-Xylene-α,α'-bis-[η⁵-(3-phenyl) -inden-1-yl] zirconium dichloride, i.e., compound of general formula (I) in which $R_2$=H, X=Cl, M=Zr, A has the structure (Ia) in which $R_1$=phenyl in 3position, $R_1$=H, in all other positions.

E) o-Xylene-α,α'-bis-[η⁵-(3,5,6-trimethyl)-inden-1-yl] zirconium dichloride, i.e., compound of general formula (I) in which $R_2$=H, X=Cl, M=Zr, A has the structure (Ia) in which $R_1$=$CH_3$ in 3-, 5- and 6-positions, $R_1$=H, in all other positions.

The characterization of the copolymers produced according to the present invention was carried out mainly by determining the propylene content in the solid polymer and the bulk viscosity, as determined by measuring Mooney viscosity on the pristine copolymer. The mechanical properties of the products were determined by submitting the copolymers to vulcanization. For all of these analyses, the corresponding method used and, when available, the method reported in technical literature, are supplied in the following.

The determination of the contents of propylene and optional diene is carried out (according to a method developed by the present Applicant) via IR on the polymers in film form with a thickness of 0.2 mm, using a Perkin-Elmer FTIR spectrophotometer model 1760 (Fourier Transform Infrared Spectroscopy).

Viscosity [Mooney viscosity (1+4)] is determined at 100° C. by using a Monsanto "1500 S" viscometer, according to ASTM method D 1646/68.

As regards the determination of the mechanical properties, these analyses were carried out on vulcanized copolymers. In the following, the vulcanization compound formulation and the dynamic-mechanical determinations carried out according to the corresponding DIN methods, are reported.

A) Vulcanization

The vulcanization compounds were prepared by using the formulation as reported in following Table 1.

TABLE 1

| INGREDIENTS | PARTS BY WEIGHT | |
|---|---|---|
| | for EPM | for EPDM |
| Polymer | 100 | 100 |
| FEF carbon black (1) | 55 | 55 |
| Zinc oxide | 5 | 5 |
| Peroximon F40 MG (2) | 5 | 5 |
| Sulfur | 0.37 | 1.5 |
| Tetramethylthiuram disulfide | — | 1.5 |
| Mercaptobenzo-thiazole | — | 0.75 |
| Paraffin Oil (3) | 30 | 30 |

(1) High Abrasion Furnace, low structure, carbon black, ex Cabot;
(2) bis-(tert.-butylperoxy-isopropyl)-benzene, masterbatch at 40% in EP copolymer, produced by Atochem.

The compound, homogenized on a roller mixer, is vulcanized between press platens under a pressure of 18 MPa and kept at 165° C. during 40 minutes.

B) Mechanical characteristics

The mechanical characteristics of the vulcanized copolymers were determined on dumb-bell specimens produced from the vulcanized slabs.

The measurement of the tensile strength was carried out according to ASTM D 412-68, of elongation at break according to ASTM D 412-68, of tension Set at 200% according to ASTM D 412-68, of Shore A hardness according to ASTM method D 2240-68.

The following examples are reported in order that the present invention may be better understood.

EXAMPLES

In the following examples, the following metallocenens of general formula (I) are used:

o-xylene-α,α'-bis-[η$^5$-(3-methyl)-inden-1-yl] zirconium dichloride, the preparation of which is disclosed in example 5 of Italian Patent Application IT-A-MI 95/A 001444 filed on Jul. 6th, 1995, indicated herein the following as "metallocene A";

o-xylene-α,α'-bis-[η$^5$-(5,6-dimethyl)-inden-1-yl] zirconium dichloride, the preparation of which is disclosed in example 7 of the above Italian Patent Application, designated herein in the following as "metallocene B";

o-xylene-α,α'-bis-[ $^5$-(4,7-dimethyl)-inden-1-yl] zirconium dichloride, the preparation of which is disclosed in example 2 of the above Italian Patent Application, designated herein in the following as "metallocene C";

o-xylene-α,α'-bis-[η$^5$-(3-methyl)-4,5,6,7-tetrahydroinden-1-yl] zirconium dichloride, referred to herein in the following as "metallocene D";

o-xylene-α,α'-bis-[η$^5$-(3,5,6-trimethyl)-4,5,6,7-tetrahydroinden-1-yl] zirconium dichloride, referred to herein in the following as "metallocene E";

o-xylene-α,α'-bis-[η-inden-1-yl] zirconium dichloride, designated herein in the following as "metallocene F", the preparation of which is disclosed in example 1 of the above Italian Patent Application,;

o-xylene-α,α'-bis-[η$^5$-(3,5,6-trimethyl)-inden-1-yl] zirconium dichloride, referred to herein in the following as "metallocene G";

o-xylene-α,α'-bis-[η$^5$-(3,4,7-trimethyl)-inden-1-yl] zirconium dichloride, referred to herein in the following as "metallocene H", not encompassed by the present invention;

o-xylene-α,α'-bis-[η$^5$-(3-ethyl)-inden-1-yl] zirconium dichloride, referred to herein in the following as "metallocene L";

o-xylene-α,α'-bis-[η$^5$-(3-phenyl)-inden-1-yl] zirconium dichloride, referred to herein in the following as "metallocene L";

EXAMPLE 1

The preparation is reported of an elastomeric copolymer according to the present invention, obtained from metallocene A and methylalumoxane, by preparing the catalytic system according to the "preliminary formation method", as discussed in the general section.

The polymerization is carried out inside a pressure reactor of 3.3 litres of capacity, thermostatted and equipped with magnetic stirring means. The reactor is purged with 1 l of anhydrous "polymerization grade" propylene containing (by weight/volume) 5% of aluminium triisobutyl (TIBA), the mixture is vented, the reaction is washed again with fresh propylene and is then emptied. By keeping temperature at 23° C., 2 litres of propylene are charged to the reactor, then 5 ml (1.5×10$^{-3}$ moles) is added of a 0.3 M solution of TIBA in hexane, and the reactor is then heated up to the polymerization temperature, of 45° C. Through a dipleg ethylene gas is injected in order to obtain an 8% concentration by mol in the liquid phase, and the mixture of monomers is kept at 45° C. during 30 minutes.

Inside a Schlenk tube, kept under nitrogen, the solution of catalyst is prepared by adding, in the order shown, 10 ml of toluene, 1.2 ml (1.82×10$^{-3}$ moles) of an 1.5 M solution of methylalumoxane Eurecene 5100 10T ex firm Witco, 0.6 ml (1.1×10$^{-6}$ moles) of an 1.9×10$^{-3}$ M solution of metallocene A in toluene. The molar ratio of aluminium:zirconium results hence to be of 1650. The so formed catalyst solution is kept at room temperature during 10 minutes and is then poured, under an inert gas flow, into a metal container from which, by means of a nitrogen overpressure, it is transferred to the reactor containing the monomers to be polymerized, caring of washing the container with 10 ml of toluene containing 1.2 ml ($1.82 \times 10^{-3}$ moles) of the same 1.5 M methylaluminoxane solution previously used. The end value of methyl alumoxane:Zr ratio results hence to be of 3300. The polymerization reaction is carried out at 45° C. caring of keeping ethylene pressure constant by continuously feeding ethylene from a cylinder charged to a balance, which allows the absorbed monomer weight to be monitored throughout the polymerization reaction. After 1 hour, ethylene feed is discontinued, the residual monomers are vented off and the autoclave is rapidly cooled down to room temperature. 185 g of polymer is recovered, with a catalyst activity of 2100 kg of polymer per g of zirconium metal. On the solid material, dried and homogenized on a roller mill, the normal physical-chemical analyses are carried out which show a propylene content in the polymer of 42%, by weight, a Mooney viscosity of >120, a weight average molecular weight ($M_w$) of $5.6 \times 10^5$ and a molecular weight dispersion ($M_w/M_n$) of 2.5.

EXAMPLES 2–11

The polymerizations have been carried out according to the operating modalities of Example 1. Test conditions and results are shown in Table 2.

The examples show that the catalytic systems obtained by starting from metallocenes according to the present invention are active to produce elastomeric ethylene-propylene copolymers with high values of Mooney viscosity.

Examples 2, 3, 5, 8–10 also show how the viscosity of the resulting elastomers can be easily controlled by using metered hydrogen amounts during the polymerization reaction.

In example 8 metallocene G is used; the synthesis of the latter is reported in the following.

Synthesis of o-xylene-α,α'-bis-[η$^5$-(3,5,6-trimethyl)-inden-1-yl] zirconium dichloride (metallocene G)

Synthesis of 1,5,6-trimethylindene

Crotonyl chloride, 140 g (1.34 moles), dissolved in 150 g (1.41 moles) of o-xylene is added to the suspension of 210 g (1.57 moles) of aluminium trichloride in 800 ml of methylene chloride, kept at the temperature of 10° C., during approximately 2 hours. When addition is complete, temperature is allowed to rise up to reach room temperature value, and the reaction mixture is kept with stirring during further 2 hours. The mixture is hydrolysed with ice-water and the organic phase is washed with water until neutral, then is dried over sodium sulfate and concentrated to dryness. The obtained residue is added to 1 l of concentrated $H_2SO_4$ and the resulting mixture is kept heated at 80° C. during 1.5 hours. After cooling, the resulting mixture is poured on ice and is extracted with ethyl ether. The ethereal phase is washed with water and then with saturated solution of sodium bicarbonate, until neutral. The resulting solution is dried over sodium sulfate and ether is evaporated off. 210 g is obtained (yield 90%) of a mixture of isomeric indanones, as a dark oil.

To the solution of 210 g of indanone derivatives dissolved in a mixture of 700 ml of THF and 350 ml of MeOH, solid sodium boron hydride (30 g) is added during 1.5 hours, with temperature being kept at 10° C. At the end, the reaction mixture is kept with stirring for a further hour. The reaction mixture is poured into ice-water and is extracted with ethyl ether. The ethereal extract is washed with water until neutral; it is then dried over sodium sulfate and the solvent is evaporated off, with 205 g being obtained of a mixture of isomeric indanols (yield 96%). The residue is crystallized by dissolving it in 1 litre of hot heptane. 786 g is obtained (yield 36%) of 3,5,6-trimethyl-1-indanol 96% pure according to chromatographic analysis.

An amount of 100 g of silica (230–400 mesh) is added to 76 g (0.432 moles) of 3,5,6-trimethyl-1-indanol, dissolved in 800 ml of toluene and 800 ml of heptane. The resulting mixture is kept refluxing for 4 hours with formed water being distilled off. At the end, the reaction mixture is filtered and silica is washed with petroleum ether. After evaporating the solvent, the residue is distilled under vacuum and the fraction boiling at 115–116° C./25 mm Hg is collected.

42 g is obtained of 1,5,6-trimethyl-indene (yield 80%).

Synthesis of α,α'-bis(3,5,6-trimethylinden-1-yl)-o-xylene 52 ml (0.130 moles) of alkyl lithium in hexane is added to a solution of 20 g (0.128 moles) of 1,5,6-trimethylindene in 200 ml of THF, during approximately 30 minutes. The resulting mixture is kept 1 hour with stirring at approximately 35° C. A yellow-green solution is obtained. Upon cooling down to −70° C., yellow lithium salt precipitates. 16.8 g (0.064 moles) of α,α'-dibromo-o-xylene dissolved in 100 ml of THF is added during about 1.5 hours. During the addition, the precipitate dissolves, and, at the end of the addition, a colourless, clear solution is obtained. Temperature is allowed to rise up to room value and the reaction mixture is allowed to stand under these conditions during 2 hours. The reaction mixture is then hydrolysed with water and extracted with ethyl ether. After water washing until neutral and after being desiccated over sodium sulfate, the ethereal extract is evaporated. 28 g is thus obtained of a colourless, thick oil. Upon crystallization at −15° C. from 100 ml of petroleum ether containing 3 ml of methanol, 15 g is obtained of α,α'-bis(3,5,6-trimethylinden-1-yl)-o-xylene. By purifying the residue obtained by evaporating mother liquors, on a silica gel column using petroleum ether as the eluent, a further 10 g is recovered of pure product (total yield 93%).

$^1$H-NMR (CDCl$_3$, δ ppm from TMS): 7.35 (m,2H) ; 7.27 (m,2H); 7.1 (s,2H); 7.0 (s,2H); 5.98 (m,2H); 3.57 (m,2H); 3.22 (m,2H); 2.55 (m,2H); 2.31 (s,6H); 2.27 (s,6H); 2.09 (m,6H).

Synthesis of o-xylene-α,α'-bis-[η$^5$-(3,5,6-trimethyl)-inden-1-yl] zirconium dichloride 23 ml (0.0368 moles) of methyllithium in ether is added to a suspension of 7.5 g (0,0179 moles) of α,α'-bis(3,5,6-trimethyl-inden-1-yl)-o-xylene in 200 ml of ethyl ether and 3 ml of THF. The resulting mixture is kept 16 hours with stirring. A whitish precipitate is formed. The resulting mixture is cooled down to −70° C. and 5.2 g of ZrCl$_4$ (0.022 moles) is then added. The reaction mixture is then allowed to heat up to reach room temperature. The colour turns from white into yellow. The resulting mixture is kept 2 hours with stirring at room temperature and is then filtered, and the solid material is washed with 50 ml of ethyl ether. The solid residue is extracted with 3×120 ml of methylene chloride. The extract is concentrated down to 20 ml, is filtered and the so recovered solid material is washed with 2×5 ml of cold methylene chloride, then with pentane, and is finally dried. 5.1 g of impure complex is obtained. The solid complex is dissolved in 100 ml of methylene chloride and the resulting mixture is filtered on celite dried at 150° C. The volume is reduced down to 20 ml, then the resulting mixture is filtered, is washed with few methylene chloride, then with pentane and is then dried. 4.0 g is obtained (yield 39%) of NMR pure complex.

$^1$H-NMR (CDCl$_3$, δ ppm from TMS): 1.80 (s,6H); 2.27 (s,6H); 2.36 (s,6H); 4.15 (dd,4H); 5.90 (bs,2H); 7.19 (s,2H); 7.25 (bs,2H); 7.37 (m,2H); 7.46 (bs,2H)

stirring means. The reactor is purged by following the same modalities as of Example 1, is charged with 2 litres of liquid propylene, 5 ml (1.5×10$^{-3}$ moles) of a 0.3 molar solution of TIBA in hexane, and is then heated up to 45° C. It is then saturated with ethylene gas, in order to obtain an ethylene concentration of 12% molar in the liquid phase and the monomers mixture is kept at 45° C. during 30 minutes.

To a Schlenk tube, kept under a flowing nitrogen stream the following are charged in the order shown: 2 ml of

TABLE 2

| Example | 2 | 3 | 4 | 5 | 6 | 7 | 8 | 9 | 10 | 11 |
|---|---|---|---|---|---|---|---|---|---|---|
| Metallocene | A | A | B | B | C | C | G | F | F | F |
| C2 % in the liquid phase | 8 | 8 | 8 | 8 | 10 | 8 | 13 | 12 | 5 | 5 |
| Temp. ° C. | 45 | 45 | 45 | 45 | 50 | 50 | 45 | 45 | 45 | 45 |
| H$_2$ mmol/t | 0.45 | 2.77 | — | 2.77 | — | — | 3.88 | 0.45 | 0.45 | — |
| Ratio of MAO/Zr | 2900 | 2900 | 3000 | 5000 | 2000 | 2000 | 4900 | 4100 | 3800 | 3800 |
| Activity kg/g Zr*h | 2600 | 2500 | 1800 | 1400 | 1180 | 900 | 6000 | 2800 | 700 | 760 |
| Propylene (% w) | 51 | 54 | 39 | 46 | 37 | 43 | 40 | 30 | 50 | 45 |
| ML (1 + 4) 100° C. | >120 | 32 | >120 | 25 | 110 | 60 | 80 | >120 | 38 | 45 |

EXAMPLE 12

An ethylene-propylene copolymerization is illustrated, which is carried out by using a catalytic system prepared by starting from metallocene C as the catalyst and alumoxane as the co-catalyst, using the "in situ" technique for preparing the catalytic system, as illustrated in the general section.

The polymerization is carried out inside an autoclave of 3.3 litres of capacity, thermostatted and equipped with magnetic stirring means. By using the same operating modalities as reported in Example 1, in the order shown the following are charged: 2 litres of liquid propylene, 1.5×10$^-$ $_3$molesof TIBA in hexane, 3.3×10$^{-3}$ moles of a solution of alumoxane Eurecene 5100 10T in toluene. The reactor is heated up to the temperature of 50° C. and ethylene gas is added until a molar concentration of 7%, is obtained in the liquid phase, and the monomer mixture is kept at 50° C. during 30 minutes.

To the so obtained mixture the following are added in the order shown: 3.3×10$^{-3}$ moles of methyl alumoxane 5100 10T and 2.2×10$^{-6}$ moles of a solution of metallocene C with a molar ratio of Al/Zr of 1500, in toluene. The polymerization reaction is carried out at 5° C. and ethylene pressure inside the reactor is kept constant as in Example 1. After 1 hour, ethylene feed is discontinued, the residual monomers are vented and autoclave is cooled down to room temperature. 150 g of polymer is recovered with a catalyst activity of 750 kg of polymer per g of zirconium metal. On the solid product, dried and homogenized on a roller mill, the normal physical-chemical analyses are carried out which show a propylene content of 51% by weight in the polymer and a Mooney viscosity of 30.

EXAMPLE 13a

An elastomeric, high viscosity copolymer is prepared by using a catalytic system formed by one of metallocenes of general formula (I), an alkylating agent and a co-catalyst of general formula (IV), according to the same modalities as discussed in the general section.

The polymerization is carried out inside an autoclave of 3.3 litres, thermostatted and equipped with a magnetic toluene, 1.1 ml (3.3×10$^{-4}$ moles) of a 3×10$^{-1}$ molar solution of TIBA in hexane and 0.6 ml (1.1×10$^{-6}$ moles) of an 1.9×10$^{-3}$ molar solution of metallocene A in toluene. The resulting solution is then kept heated at 40° C. during 1 hour with stirring and 8 ml of toluene and 1.3 ml (3.3×10$^{-6}$ moles) of a 2.5×10$^{-3}$ molar solution of N,N'-dimethylanilinaluminium tetra-(pentafluorophenyl)-borate in toluene, are then added to it. The molar ratio of alkylating compound (TIBA) to metallocene A results to be 300 and the ratio of compound of general formula (IV) to metallocene A results to be 3. The so obtained solution is immediately transferred under nitrogen to the previously prepared polymerization reactor. Ethylene pressure inside the reactor is kept constant by means of a continuous feed from a cylinder charged on a balance, which makes it possible the absorbed monomer weight to be monitored throughout the reaction. After 1 hour of polymerization, ethylene feed is discontinued, the residual monomers are vented and autoclave is cooled down to room temperature. 130 g of polymer is recovered, with a catalyst activity of 1300 kg of polymer per g of zirconium metal. On the solid material, dried and homogenized on a roller mill, the normal physical-chemical analyses are carried out which show a propylene content of 39%, by weight, in the polymer, and a Mooney viscosity of 62.

EXAMPLE 13b

An elastomeric, high Mooney viscosity, copolymer is prepared by using a catalytic system formed by metallocene A, TIBA as the alkylating agent, and the co-catalyst of general formula (VII) (C$_6$H$_5$)$_3$CB(C$_6$F$_5$)$_4$, according to the same modalities as indicated in Example 13a.

From the polymerization reaction, 160 g of polymer is recovered, with a yield of 1600 kg of polymer per g of zirconium metal.

On the solid material, dried and homogenized on a roller mill, the normal physical-chemical analyses are carried out which show a propylene content of 39%, by weight, in the polymer, a Mooney viscosity of 42.

EXAMPLE 14A

Preparation of o-xylene-α,α'-bis-[η$^5$-(3-methyl)-4,5, 6,7-tetrahydroinden-1-yl] zirconium dichloride (metallocene D)

o-Xylene-α,α'-bis-[η$^5$-(3-methyl)-inden-1-yl] zirconium dichloride, i.e., metallocene A, is prepared by operating as disclosed in Example N. 5 of Italian Patent Application IT-A-MI 95/A 001444,.

An amount of 1.1 g of this complex is dissolved in 50 ml of anhydrous $CH_2Cl_2$ containing 60 mg of $PtO_2$ and 3 A molecular sieves. The resulting suspension is charged to a pressure reactor and is hydrogenated under a hydrogen pressure of 10 MPa at 20° C. during 20 hours. By adding heptane, 0.85 g (yield 77%) of metallocene D is obtained.

$^1$H-NMR ($CDCl_3$, δ ppm from TMS): 7.20 (m,4H,Ar); 5.55 (s,2H); 3.70 (dd,4H) 2.9–2.3 (m,8H); 2.0 (s,6H); 1.8–1.5 (m,8H).

$^{13}$C-NMR ($CDCl_3$, δ ppm from TMS): 137.81; 132.89; 131.87; 127.75; 123.68; 120.98; 118.26; 32.48; 25.27; 24.54; 23.18; 22.82; 14.06.

EXAMPLE 14b

Copolymerizations in the Presence of Metallocene D

By operating according to the same modalities as reported as in Example 1, to the reactor the following are charged: 2 litres of liquid propylene, then ethylene is added in order to obtain a liquid phase containing a molar ethylene content of 10%, and finally $1.5 \times 10^{-3}$ moles of TIBA is added, with the reactor being then kept at 40° C. during 30 minutes. The catalyst is prepared by starting from 20 ml of toluene, $9.2 \times 10^{-4}$ moles of methylalumoxane Eurecene 5100 10T and $1.7 \times 10^{-7}$ moles of metallocene D, by using the same procedure as specified in Example 1. Finally, $1.11 \times 10^{-3}$ moles of hydrogen gas is added and the reaction polymerization is carried out at 40° C. during 1 hour. Conditions and results are reported in Table 3.

This example shows how a metallocene of general formula (I) having the A radical of (Ib) structure is capable of producing high Mooney viscosity elastomeric copolymers in high yield.

EXAMPLE 15a

Preparation of o-xylene-α,α'-bis-[η$^5$-(3,5,6-trimethyl)-4, 5,6,7-tetrahydroinden-1-yl] zirconium dichloride (metallocene E)

1.2 g of o-xylene-α,α'-bis-[η$^5$-(3,5,6-trimethyl)-4,5,6,7-tetrahydroinden-1-yl] zirconium dichloride dissolved in 50 ml of methylene chloride containing 50 mg of $PtO_2$ and 0.5 g of 4A molecular sieves is charged to an autoclave under 9.5 MPa of hydrogen during 3 days. At the end, the solution is filtered, is concentrated down to 20 ml and 50 ml of heptane is then added and the solution is concentrated once more down to 10 ml. The formed precipitate is filtered off, washed with pentane and dried; 0.8 g of complex is obtained the NMR spectra is the following:

$^1$H-NMR ($CDCl_3$, δ ppm from TMS): 7.22 (m); 5.71 (s); 5.50 (s,1H); 3.79 (m); 2.5 (m); 2.0 (s,3H); 1.95 (s,3H); 1.9–1.4 (m); 1.04 (d,3H); 0.98 (d,3H); 0.92 (d,3H); 0.9 (d,3H).

EXAMPLE 15b

Copolymerization in the presence of Metallocene E

By operating according to the same modalities as reported as in Example 1, to the polymerization reactor the following are charged: 2 litres of liquid propylene, then ethylene is added in order to obtain a liquid phase containing 8% of ethylene by mol, and finally $1.5 \times 10^{-3}$ moles of TIBA is added, with the reactor being then kept at 45° C. during 30 minutes. The catalyst is prepared by starting from 20 ml of toluene, $3.6 \times 10^{-3}$ moles of metallocene E, by using the same procedure as specified in Example 1. The polymerization is carried out at 45° C. during 1 hour. Conditions and results are reported in Table 3.

This example shows how a metallocene of general formula (I) the A radical of which has the (Ib) structure is capable of producing high Mooney viscosity elastomeric copolymers in high yield.

COMPARISON EXAMPLES 16a–b

Copolymerization in the Presence of Metallocene H. Polymerization 16a

By operating according to the same modalities as reported as in Example 1, to the polymerization reactor the following are charged: 2 litres of liquid propylene, then ethylene is added in order to obtain a liquid phase containing a molar ethylene content of 8%, and finally $1.5 \times 10^{-3}$ moles of TIBA is added, with the reactor being then kept at 45° C. during 30 minutes.The catalyst is prepared by starting from 20 ml of toluene, $6.0 \times 10^{-3}$ moles of methylalumoxane Eurecene 5100 10T and $2.0 \times 10^{-6}$ moles of metallocene H, by using the same procedure as specified in Example 1. The polymerization is carried out at 45° C. during 1 hour. Conditions and results are reported in Table 3.

Polymerization 16b.

By operating according to the same modalities as reported in Example 1, to the polymerization reactor the following are charged: 2 litres of liquid propylene, then ethylene is added in order to obtain a liquid phase containing a molar ethylene content of 8%, and finally $1.5 \times 10^{-3}$ moles of TIBA is added, with the reactor being then kept at 40° C. during 30 minutes. The catalyst is prepared by starting from 20 ml of toluene, $6.0 \times 10^{-3}$ moles of methylalumoxane Eurecene 5100 10T and $2.0 \times 10^{-6}$ moles of metallocene H, by using the same procedure as specified in Example 1. The polymerization is carried out at 40° C. during 1 hour. Conditions and results are reported in Table 3.

The data relating to the comparison examples 16a–b reported in table 3 set forth how a catalytic system obtained by starting from a metallocene of general formula (I) in which all $R_2$ radicals are H and with the A radical having the general formula (Ia) in which $R_1$ radicals in 3-, 4- and 7- positions are —$CH_3$, with the residual $R_1$'s being all —H, is not capable to produce elastomeric polymers having a high enough Mooney viscosity.

EXAMPLE 17

An elastomeric copolymer is produced according to the process of the present invention, using metallocene I, the preparation of which is reported in the following.

Synthesis of o-xylene-α,α'-bis-[η$^5$-(3-ethyl)-inden-1-yl] zirconium dichloride (metallocene I)

To a solution of 30 ml (0.26 moles) of indene in 250 ml of THF, 105 ml is added (0.26 moles) of 2.5 M BuLi in hexane, with temperature being kept comprised within the range of from 30° C. to 40° C. The reaction mixture is then cooled down to −70° C. and 19 ml (0.25 moles) of ethyl bromide is added dropwise during approximately 3 hours. The temperature is allowed to rise up to approximately 20–25° C. and then the mixture is hydrolysed with water and extracted with petroleum ether. After washing until neutral, drying and evaporation of the organic phase, the obtained residue is distilled. The fraction boiling at 92–95° C./30 mm Hg is collected, and 28 g of 1-ethylindene is obtained (yield 78%)

To a solution of 20 g (0.138 moles) of 1-ethylindene in 200 ml of THF a solution is added of 56 ml (0.14 moles) of 2.5 M BuLi in hexane, with temperature being kept within the range of from 30 to 40° C. The reaction mixture is then cooled down to −70° C. and 75 ml is added dropwise of a solution of 16.5 g (0.062 moles) of α,α'-dibromo-o-xylene in THF, during about 3 hours. The temperature is allowed to rise up to 20–30° C., the mixture is hydrolysed with water and the hydrolysed mixture is extracted with petroleum ether. After washing until neutral, drying and evaporation of the organic phase, the residue is purified by eluting it on a silica gel column using petroleum ether as the eluent. 2.7 g is obtained (yield 89%) of o-xylene-α,α'-bis-(3-ethyl-1-indene), as an oil.

$^1$H-NMR (CDCl$_3$, δ ppm from TMS): 7.45–7.1 (m,12H); 6.2–5.9 (m,2H); 3.9 (m,2H); 3.7 (m,1H); 3.35 (m,1H); 3.2 (m,1H); 2.5–2.7 (m,3H); 1.9 (m,H); 1.5 (m,1H); 1.25 (m,4H); 0.9 (m,4H).

To the suspension of 8.4 g (0.0215 moles) of -oxylene-α,α'-bis-(3-ethyl-1-indene) in 200 ml of ethyl ether, 27 ml (0.043 moles) is added of a 1.6 M solution of methyl lithium. The mixture is kept with stirring for 16 hours. A white precipitate is formed. The solution is cooled down to −70° C. and 8.0 g (0.034 moles) of solid ZrCl$_4$ is added. The resulting mixture is kept 2 hours with stirring at room temperature and is then filtered, and the recovered solid material is washed with 50 ml of ethyl ether. The solid residue is extracted with 3×120 ml of methylene chloride. The solvent is evaporated off and then 100 ml of ethyl ether is added, and the solid residue is triturated well. The mixture is filtered and the recovered solid material is washed with pentane and then is dried. 4.8 g is obtained of impure complex. The solid material is dissolved in 100 ml of methylene chloride and is filtered over celite desiccated at 150° C. The volume is reduced down to 50 ml and then pentane is added in order to precipitate the product. 2.0 g is obtained of a solid material which, when dissolved in methylene chloride, yields a hazy solution; by adding pentane to mother liquors 1.1 g (yield 9% of complex of NMR pure complex is obtained.

$^1$H-NMR (CDCl$_3$, δ ppm from TMS): 7.55 (m,4H); 7.45 (m,4H); 7.29 (m,2H); 7.15 (m,2H); 6.0 (b,2H); 4.3 (m,4H); 2.64 (m,2H); 2.0 (m,2H); 1.0 (t,6H).

Polymerizations in the Presence of Metallocene I

By operating according to the same modalities as reported as in Table 1, to the reactor 2 litres are charged of liquid propylene and ethylene gas in order to obtain a molar ethylene content in liquid phase of 8%, and $1.5 \times 10^{-3}$ moles of TIBA, with the reactor being then kept at 45° C. during 30 minutes. The catalyst is prepared by starting from 20 ml of toluene, $6.0 \times 10^{-3}$ moles of methylalumoxane Eurecene 5100 10T and $2.0 \times 10^{-6}$ moles of metallocene I, by using the same procedure as specified in Example 1. Finally, $2.77 \times 10^{-3}$ moles of hydrogen gas is added and the reaction polymerization is carried out at 45° C. during 1 hour. Conditions and results are reported in Table 3.

This example shows how the catalytic system obtained by starting from a metallocene of general formula (I) in which all R$_2$'s are H and with the A radical of structure (Ia) having R$_1$ in 3-position equal to ethyl and all other R$_1$'s equal to H, is capable of producing high Mooney viscosity elastomeric copolymers in high yield.

EXAMPLE 18

An elastomeric copolymer is obtained according to the present invention by using metallocene L, the preparation of which is reported in the following.

Synthesis of o-xylene-α,α'-bis-[η$^5$-(3-phenyl)-inden-1-yl] zirconium dichloride (metallocene L)

a) Synthesis of 1-phenylindene

To the solution of 90 g (0.0608 moles) of cinnamic acid in 400 ml of benzene 300 g (2.25 moles) of aluminium trichloride is added, beginning with a very slow addition rate. At the end, the mixture is kept refluxing for 22 hours. The resulting reaction mixture is hydrolysed with ice and is extracted with ethyl ether which is washed first with water until neutral, and then with a solution of 10% sodium hydroxide. The organic extract is then desiccated and evaporated. The residue is triturated with petroleum ether, is then filtered and is then washed with a small amount of diisopropyl ether, then once more with petroleum ether and is dried yielding 76 g (yield of 60%) of 3-phenyl-1-indanone.

Keeping the temperature at −5° C., to a suspension of 5.0 g (0.131 moles) of LiAlH$_4$ in 300 ml of ethyl ether, 35 g (0.168 moles) is added of 3-phenyl-1-indanone dissolved in 50 ml of THF. The oil obtained by evaporating ether (40 g), is dissolved in 300 ml of toluene containing 20 g of SiO$_2$ and kept refluxing for 2 hours, with formed water being distilled off. The resulting mixture is filtered, the solvent is evaporated and by distillation 18 g is obtained (yield of 50%) of 1-phenylindene boiling at 95–100° C./0.2 mm Hg.

b) Synthesis of o-xylene-α,α'-bis-(3-phenyl-1-indene)

To a solution of 16 g (0.0833 moles) of 1-phenylindene in 200 ml of THF, 34 ml (0.085 moles) is added of 2.5 M BuLi in hexane. The resulting mixture is cooled down to −70° C. and 1 g (0.041 moles) is added dropwise of α,α'-dibromo-o-xylene. The mixture is allowed to reach room temperature, then is hydrolysed with water and extracted with ethyl ether. The organic phase is washed until neutral, is then dried and evaporated. By purification on a silica gel column with petroleum ether as the eluent, 18 g of product is obtained (yield of 90%)

$^1$H-NMR (CDCl$_3$, δ ppm from TMS): 7.80–7.0 (m,22H); 6.75 (m,1H); 6.5 (m,1H); 4.2–4.4 (m,6H).

c) Synthesis of o-xylene-α,α'-bis-[η$^5$-(3-phenyl)-inden-1-yl] zirconium dichloride (metallocene L)

To a suspension of 9.0 g (0.0185 moles) of o-xylene-α,α'-bis-(3-phenyl)-1-indene in 200 ml of ethyl ether, 24 ml is added of a 1.6 M solution of methyllithium in ethyl ether (0.038 moles). The resulting mixture is kept with stirring for 16 hours. A white precipitate forms. The reaction mixture is cooled down to −70° C. and then 5.5 g (0.024 moles) of solid ZrCl$_4$ is added. The reaction mixture is then allowed to reach room temperature and is kept with stirring for 2 hours, is then filtered and the collected solid material is washed with 50 ml of ethyl ether. The solid residue is extracted with 3×120 ml of methylene chloride. The solvent is evaporated off and 100 ml of ethyl ether is added, while carefully triturating the solid material. The resulting mixture is filtered and the collected solid is washed with pentane and is then desiccated. 4.8 g of impure complex is obtained. The solid material is dissolved in 100 ml of methylene chloride and is filtered on celite desiccated at 150° C. The volume is reduced down to 50 ml, then pentane is added in order to precipitate the product. 2.0 g is obtained of a solid product which, when dissolved in methylene chloride, yields a hazy solution. By adding pentane to mother liquors 1.2 g is obtained (yield of 10%) of NMR pure complex.

$^1$H-NMR (CDCl$_3$, δ ppm from TMS): 7.6–6.9 (m,22H); 6.64 (bs,1H); 6.4 (bs,1H); 4.44 (d,2H); 4.28 (d,2H).

d) Polymerization in the Presence of Metallocene L

By operating according to the same modalities as reported in Table 1, to the reactor 2 litres of liquid propylene and ethylene gas are charged in order to obtain a molar ethylene content in liquid phase of 8%, and $1.5 \times 10^{-3}$ moles of TIBA, with the reactor being then kept at 45° C. during 30 minutes. The catalyst is prepared by starting from 20 ml of toluene, $6.0 \times 10^{-3}$ moles of methylalumoxane Eurecene 5100 10T and $2.0 \times 10^{-6}$ moles of metallocene L, by using the same procedure as specified in Example 1. Finally, $1.11 \times 10^{-3}$ moles of hydrogen gas is added and the reaction polymerization is carried out at 45° C. during 1 hour. Conditions and results are reported in Table 3.

This example shows how the catalytic system obtained by starting from a metallocene of general formula (I) in which all $R_2$'s are H and with the A radical of structure (Ia) having $R_1$ radical in 3-position equal to —$C_6H_5$ and all other $R_1$'s equal to H, is capable of producing high Mooney viscosity elastomeric copolymers in high yield.

TABLE 3

| Example | 14b | 15b | Comp. 16a | Comp. 16b | 17 | 18 |
| --- | --- | --- | --- | --- | --- | --- |
| Metallocene | D | E | H | H | I | L |
| C2 % in the liquid phase | 10 | 12 | 8 | 8 | 8 | 8 |
| Temp. ° C. | 40 | 45 | 45 | 40 | 45 | 45 |
| H$_2$ mmol/t | 1.11 | — | — | — | 2.77 | 1.11 |
| Ratio of MAO/Zr | 5400 | 3000 | 3100 | 3000 | 3800 | 3000 |
| Activity kg/g Zr*h | 3900 | 1000 | 300 | 500 | 1200 | 500 |
| Propylene (% w) | 50 | 30 | 56 | 45 | 47 | 36 |
| ML (1 + 4) 100° C. | 60 | 20 | <10 | 10 | 26 | 25 |

EXAMPLE 19

An ethylene/propylene/diene terpolymer is prepared by using a catalytic system consisting of metallocene E and using 1,4-hexadiene as the diene. The example shows as, in accordance with the present invention, ethylene/propylene copolymers containing unsaturation to be used in elastomer curing can be prepared.

By operating according to the same modalities as reported in Example 1, to the reactor the following ingredients are charged: 2 litres of liquid propylene, 26 ml of 1,4-hexadiene and 5 ml ($1.5 \times 10^{-3}$ moles) of a 0.3 molar TIBA solution in hexane. The reactor is then heated up to the desired polymerization temperature of 45° C. and ethylene gas is added in order to obtain a molar ethylene content in the liquid phase of 10% and the monomers mixture is kept at 45° C. during 30 minutes.

The catalyst solution is then added which is obtained by mixing 10 ml of toluene, $1.4 \times 10^{-3}$ moles of Eurecene 5100 10T and $6.9 \times 10^{-7}$ moles of metallocene G. The container is washed with 10 ml of toluene containing a further amount of $1.4 \times 10^{-3}$ moles of Eurecene 5100 10T, with a molar ratio of Al:Zr of 400 being thus obtained in the reactor. To the reactor $2.77 \times 10^{-3}$ moles of hydrogen is added and the polymerization is then carried out at 45° C. during 1 hour and, at the end, 83 g of polymer is recovered, which corresponds to a catalyst activity of 1200 kg of polymer per g of zirconium metal. On the resulting solid product, dried and homogenized on a roller mill the normal physical-chemical analyses are carried out which display a propylene content of 42% by weight in the polymer, a Mooney viscosity of 35 and a content of copolymerized 1,4-hexadiene of 3.0% by weight.

EXAMPLE 20

The mechanical properties are determined of the polymers prepared in Examples 2, 3, 6 and 7.

By operating according to the previously reported vulcanization formulation, vulcanized compounds were prepared using, in each case, 100 g of polymer. After vulcanization, specimens were obtained from the materials, the mechanical properties of which, as determined according to the modalities as indicated in the general section, are reported in following Table 4.

TABLE 4

| Polymer | Tensile strength (MPa) | Elongation at break (MPa) | Tension set 200% % | Shore A hardness |
| --- | --- | --- | --- | --- |
| Ex. 2 | 11.8 | 441 | 5 | 52 |
| Ex. 3 | 8.9 | 692 | 7 | 47 |
| Ex. 6 | 15.2 | 440 | 8 | 54 |
| Ex. 7 | 9.4 | 650 | 8 | 41 |

The data of Table 4 show how the polymers obtained according to the operating modalities according to the present invention display values of tensile strength, elongation at break, deformation and hardness, which are typical of elastomeric materials.

We claim:

1. A process for preparing elastomeric ethylene-propylene (EPM) copolymers or elastomeric ethylene-propylene-diene (EPDM) terpolymers having a propylene content of from 15 to 75% by weight, comprising:

(1) feeding propylene and, optionally, diene, to polmerization reactor under a pressure where the propylene is a liquid;

(2) adding ethylene to the propylene;

(3) adding a catalytic system which comprises
      (a) one or more metallocenes represented by formula (I):

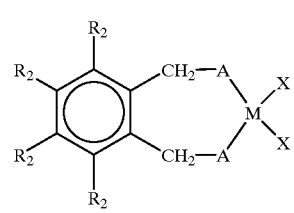

(I)

wherein
   M is zirconium;
   X is chlorine;
   A is a $\eta^5$-indenyl radical represented by formula (Ia) or a $\eta^5$-tetrahydroindenyl radical represented by formula (Ib):

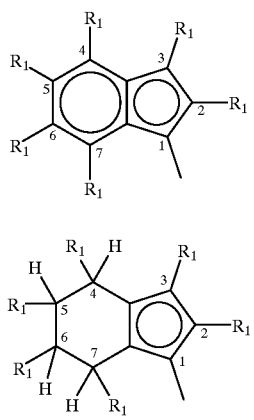

wherein $R_1$ and $R_2$, which may be the same or different from each other, are selected from the group consisting of H, aliphatic radicals, cycloaliphatic radicals, and aryl radicals, with the proviso that compounds in which A is represented by formula (Ia), $R_2$=H and $R_1$ is different from —H in the 3-, 4- and 7-positions, are excluded, and (b) one or more co-catalysts selected from the group consisting of (i) compounds represented by the formula (IV) $(Ra)_x NH_{4-x} B(Rd)_4$, compounds represented by the formula (V) $(Ra)_3 PHB(Rd)_4$, compounds represented by the formula (VI) $B(Rd)_3$, compounds represented by the formula (VII) $(C_6H_5)_3 CB(Rd)_4$, optionally in the presence of an alkylating agent, wherein x is 1, 2, or 3, wherein each Ra is independently selected from the group consisting of monofunctional alkyl radicals and monofunctional aryl radicals, and wherein each Rd is independently a monofunctional aryl radical which may be partially or totally fluorinated, and (ii) alumoxanes;

(4) polymerizing the propylene, the ethylene, and, optionally, the diene, for a time sufficient to produce a EP(D)M copolymer having a Mooney viscosity ($ML_{1+4}$ at 100° C.) higher than 20.

2. The process of claim 1, wherein the elastomeric ethylene-propylene copolymers (EPM) or the elastomeric ethylene-propylene-diene terpolymers (EPDM) have a propylene content of from 25 to 70%.

3. The process of claim 2, wherein the propylene content is from 35 to 60% by weight.

4. The process of claim 1, wherein the elastomeric ethylene-propylene-diene terpolymers (EPDM) have a diene content of at most 15% by weight.

5. The process of claim 4, wherein the diene content is from 2 to 10% by weight.

6. The process of claim 1, wherein $R_1$ and $R_2$, which may be the same or different from each other, are selected from the group consisting of hydrogen, methyl, ethyl, and phenyl.

7. The process of claim 1, wherein each $R_2$'s is —H, and in the A radical the number of $R_1$'s different from —H is equal to, or lower than, 3.

8. The process of claim 1, wherein the metallocene represented by formula (I) is selected from the group consisting of:

o-xylene-α,α'-bis-[$\eta^5$-(3-methyl)-inden-1-yl] zirconium dichloride, o-xylene-α,α'-bis-[$\eta^5$-(5,6-dimethyl)-inden-1-yl] zirconium dichloride, o-xylene-α,α'-bis-[$\eta^5$-(4,7-dimethyl)-inden-1-yl] zirconium dichloride, o-xylene-α,α'-bis-[$\eta^5$-(3-methyl)-4,5,6,7-tetrahydroinden-1-yl] zirconium dichloride, o-xylene-α,α'-bis-[$\eta^5$-(3,5,6-trimethyl)-4,5,6,7-tetrahydroinden-1-yl] zirconium dichloride, o-xylene-α,α'-bis-[$\eta^5$-inden-1-yl] zirconium dichloride, o-xylene-α,α'-bis-[$\eta^5$-(3,5,6-trimethyl)-inden-1-yl] zirconium dichloride, o-xylene-α,α'-bis-[$\eta^5$-(3-ethyl)-inden-1-yl] zirconium dichloride, o-xylene-α,α'-bis-[$\eta^5$-(3-phenyl)-inden-1-yl] zirconium dichloride, and o-xylene-α,α'-bis-[$\eta^5$-4,5,6,7-tetrahydroinden-1-yl] zirconium dichloride.

9. The process of claim 1, wherein the propylene and, optionally, the diene, are diluted with a hydrocarbon in (1).

10. The process of claim 9, wherein the hydrocarbon is a low boiling $C_3$–$C_5$-hydrocarbon.

11. The process of claim 10, wherein the hydrocarbon is propane.

12. The process of claim 1, wherein the polymerization temperature is from −78° C. up to 200° C., and the polymerization pressure is from atmospheric pressure up to 50 kg/cm²G.

13. The process of claim 12, wherein the polymerization temperature is from −20° C. up to 100° C.

14. The process of claim 13, wherein the polymerization temperature is from 10° C. up to 70° C.

15. The process of claim 1, wherein the co-catalyst is an alumoxane, and the molar ratio of aluminium:metallocene is from $5 \times 10^2$ to $2 \times 10^4$.

16. The process of claim 1, wherein the concentration of the metallocene represented by formula (I) in the reaction mixture is from $10^{-8}$ up to $10^{-4}$ mole/liter.

* * * * *